(12) United States Patent
Robinson et al.

(10) Patent No.: US 9,411,934 B2
(45) Date of Patent: Aug. 9, 2016

(54) IN-ROOM ALARM CONFIGURATION OF NURSE CALL SYSTEM

(75) Inventors: Andrew S. Robinson, Durham, SC (US); Richard J. Schuman, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 264 days.

(21) Appl. No.: 13/466,262

(22) Filed: May 8, 2012

(65) Prior Publication Data
US 2013/0300548 A1 Nov. 14, 2013

(51) Int. Cl.
| G09F 25/00 | (2006.01) |
| G08B 9/00 | (2006.01) |
| G08B 13/02 | (2006.01) |
| G08B 27/00 | (2006.01) |
| G08B 5/00 | (2006.01) |
| G08B 5/36 | (2006.01) |
| B61L 25/08 | (2006.01) |
| G05B 11/01 | (2006.01) |
| G08C 19/16 | (2006.01) |
| G06F 19/00 | (2011.01) |
| A61B 5/00 | (2006.01) |

(52) U.S. Cl.
CPC ............... *G06F 19/327* (2013.01); *A61B 5/002* (2013.01)

(58) Field of Classification Search
CPC .. A61B 5/0002; A61B 5/1115; A61B 5/7435; A61B 5/1117; A61B 2560/0271; A61B 5/0006; A61B 5/742; A61B 2562/0295; A61B 5/14532; A61B 5/15003; A61B 5/150221; A61B 5/150236; G08B 1/00; G08B 21/043; G08B 25/016; G06F 19/3418; G06F 19/327; G06F 19/3487; G06F 19/3406; G06F 19/322; A61M 16/0463; A61M 2230/04; A61M 25/007; A61M 25/10; G06Q 50/22; G06Q 50/24
USPC ................................................... 340/286.07
See application file for complete search history.

(56) References Cited

U.S. PATENT DOCUMENTS

| 2,330,356 A | 9/1943 | Belliveau |
| 2,335,524 A | 11/1943 | Lomax |
| 2,736,888 A | 2/1956 | McLain |
| 2,896,021 A | 7/1959 | Philipps |

(Continued)

FOREIGN PATENT DOCUMENTS

| WO | WO 02/091297 | 11/2002 |
| WO | WO 2004/036390 | 4/2004 |

OTHER PUBLICATIONS

Author: Wondka, Date: Dec. 19, 2011, Pertinent Pages. the whole document.*

(Continued)

*Primary Examiner* — Steven Lim
*Assistant Examiner* — Muhammad Adnan
(74) *Attorney, Agent, or Firm* — Barnes & Thornburg LLP

(57) ABSTRACT

A nurse call system includes a room station located in a patient room and having a graphical display. The nurse call system also includes an equipment port located in the patient room and configured to couple to medical equipment to receive an alarm signal from the medical equipment. The room station is configured to present a list of medical equipment types on the second graphical display in response to coupling of the medical equipment to the equipment port for selection by a user of the type of medical equipment coupled to the equipment port.

21 Claims, 6 Drawing Sheets

(56) References Cited

U.S. PATENT DOCUMENTS

| | | | |
|---|---|---|---|
| 3,098,220 A | 7/1963 | De Graaf | |
| 3,439,320 A | 4/1969 | Ward | |
| 3,478,344 A | 11/1969 | Schwitzgebel et al. | |
| 3,553,383 A | 1/1971 | Rochtus | |
| 3,599,199 A | 8/1971 | Bunting | |
| 3,599,200 A | 8/1971 | Bunting | |
| 3,696,384 A | 10/1972 | Lester | |
| 3,739,329 A | 6/1973 | Lester | |
| 3,767,859 A | 10/1973 | Doering et al. | |
| 3,805,265 A | 4/1974 | Lester | |
| 3,913,153 A | 10/1975 | Adams et al. | |
| 3,973,200 A | 8/1976 | Akerberg | |
| 4,067,005 A | 1/1978 | Levy et al. | |
| 4,150,284 A | 4/1979 | Trenkler et al. | |
| 4,151,407 A | 4/1979 | McBride et al. | |
| 4,183,015 A | 1/1980 | Drew et al. | |
| 4,216,462 A | 8/1980 | McGrath et al. | |
| 4,225,953 A | 9/1980 | Simon et al. | |
| 4,228,426 A | 10/1980 | Roberts | |
| 4,237,344 A | 12/1980 | Moore | |
| 4,264,982 A | 4/1981 | Sakarya | |
| 4,275,385 A | 6/1981 | White | |
| 4,279,433 A | 7/1981 | Petaja | |
| 4,298,863 A | 11/1981 | Natitus et al. | |
| 4,331,953 A | 5/1982 | Blevins et al. | |
| 4,356,475 A | 10/1982 | Neumann et al. | |
| 4,418,334 A | 11/1983 | Burnett | |
| 4,455,548 A | 6/1984 | Burnett | |
| 4,489,387 A | 12/1984 | Lamb et al. | |
| 4,495,495 A | 1/1985 | Ormanns et al. | |
| 4,495,496 A | 1/1985 | Miller, III | |
| 4,539,560 A | 9/1985 | Fleck et al. | |
| 4,577,185 A | 3/1986 | Andersen | |
| 4,578,671 A | 3/1986 | Flowers | |
| 4,593,273 A | 6/1986 | Narcisse | |
| 4,598,275 A | 7/1986 | Ross et al. | |
| 4,601,064 A | 7/1986 | Shipley | |
| 4,649,385 A | 3/1987 | Aires et al. | |
| 4,680,790 A | 7/1987 | Packard et al. | |
| 4,709,330 A | 11/1987 | Yokoi et al. | |
| 4,740,788 A | 4/1988 | Konneker | |
| 4,752,951 A | 6/1988 | Konneker | |
| 4,792,798 A | 12/1988 | Wilowski | |
| 4,795,905 A | 1/1989 | Zierhut | |
| 4,814,751 A | 3/1989 | Hawkins et al. | |
| 4,833,452 A | 5/1989 | Currier | |
| 4,833,467 A | 5/1989 | Kobayashi et al. | |
| 4,837,568 A | 6/1989 | Snaper | |
| 4,853,692 A | 8/1989 | Wolk et al. | |
| 4,899,135 A | 2/1990 | Chahariiran | |
| 4,947,152 A | 8/1990 | Hodges | |
| 4,955,000 A | 9/1990 | Nastrom | |
| 4,967,195 A | 10/1990 | Shipley | |
| 4,990,892 A | 2/1991 | Guest et al. | |
| 4,998,095 A | 3/1991 | Shields | |
| 4,998,939 A | 3/1991 | Potthast et al. | |
| 5,006,830 A | 4/1991 | Merritt | |
| 5,027,314 A | 6/1991 | Linwood et al. | |
| 5,041,086 A | 8/1991 | Koenig et al. | |
| 5,062,151 A | 10/1991 | Shipley | |
| 5,065,154 A | 11/1991 | Kaiser | |
| 5,086,290 A | 2/1992 | Murray et al. | |
| 5,103,108 A | 4/1992 | Crimmins | |
| 5,124,991 A | 6/1992 | Allen | |
| 5,137,033 A | 8/1992 | Norton | |
| 5,153,584 A | 10/1992 | Engira | |
| 5,262,944 A | 11/1993 | Weisner et al. | |
| 5,266,944 A | 11/1993 | Carroll et al. | |
| 5,291,399 A | 3/1994 | Chaco | |
| 5,319,355 A | 6/1994 | Russek | |
| 5,319,363 A | 6/1994 | Welch et al. | |
| 5,357,254 A | 10/1994 | Kah, Jr. | |
| 5,375,604 A | 12/1994 | Kelly et al. | |
| 5,396,224 A | 3/1995 | Dukes et al. | |
| 5,396,227 A | 3/1995 | Carroll et al. | |
| 5,416,695 A | 5/1995 | Stutman et al. | |
| 5,434,775 A | 7/1995 | Sims et al. | |
| 5,446,678 A | 8/1995 | Saltzstein et al. | |
| 5,455,560 A | 10/1995 | Owen | |
| 5,458,123 A | 10/1995 | Unger | |
| 5,461,390 A | 10/1995 | Hoshen | |
| 5,475,367 A | 12/1995 | Prevost | |
| 5,534,851 A * | 7/1996 | Russek | 340/573.4 |
| 5,537,459 A | 7/1996 | Price et al. | |
| 5,548,637 A | 8/1996 | Heller et al. | |
| 5,549,113 A | 8/1996 | Halleck et al. | |
| 5,561,412 A * | 10/1996 | Novak et al. | 340/286.07 |
| 5,568,119 A | 10/1996 | Schipper et al. | |
| 5,576,452 A | 11/1996 | Dever et al. | |
| 5,576,952 A | 11/1996 | Stutman et al. | |
| 5,579,001 A | 11/1996 | Dempsey et al. | |
| 5,588,005 A | 12/1996 | Ali et al. | |
| 5,594,786 A | 1/1997 | Chaco et al. | |
| 5,621,388 A | 4/1997 | Sherburne et al. | |
| 5,635,907 A | 6/1997 | Bernard et al. | |
| 5,636,245 A | 6/1997 | Ernst et al. | |
| 5,640,953 A | 6/1997 | Bishop et al. | |
| 5,650,769 A | 7/1997 | Campana, Jr. | |
| 5,650,770 A | 7/1997 | Schlager et al. | |
| 5,664,270 A | 9/1997 | Bell et al. | |
| 5,682,139 A | 10/1997 | Pradeep et al. | |
| 5,686,888 A | 11/1997 | Welles, II | |
| 5,686,902 A | 11/1997 | Reis et al. | |
| 5,687,734 A | 11/1997 | Dempsey et al. | |
| 5,689,229 A | 11/1997 | Chaco et al. | |
| 5,691,980 A | 11/1997 | Welles, II et al. | |
| 5,699,038 A | 12/1997 | Ulrich et al. | |
| 5,705,980 A | 1/1998 | Shapiro | |
| 5,708,421 A | 1/1998 | Boyd | |
| 5,713,856 A | 2/1998 | Eggers et al. | |
| 5,719,761 A | 2/1998 | Gatti et al. | |
| 5,731,757 A | 3/1998 | Layson, Jr. | |
| 5,742,237 A | 4/1998 | Bledsoe | |
| 5,751,246 A | 5/1998 | Hertel | |
| 5,752,917 A | 5/1998 | Fuchs | |
| 5,760,704 A | 6/1998 | Barton et al. | |
| 5,767,791 A | 6/1998 | Stoop et al. | |
| 5,781,442 A | 7/1998 | Engleson et al. | |
| 5,793,290 A | 8/1998 | Eagleson et al. | |
| 5,808,564 A | 9/1998 | Simms et al. | |
| 5,812,056 A | 9/1998 | Law | |
| 5,822,418 A | 10/1998 | Yacenda et al. | |
| 5,822,544 A | 10/1998 | Chaco et al. | |
| 5,838,223 A | 11/1998 | Gallant et al. | |
| 5,844,488 A | 12/1998 | Musick | |
| 5,867,821 A | 2/1999 | Ballantyne et al. | |
| 5,877,675 A | 3/1999 | Rebstock et al. | |
| 5,933,488 A | 8/1999 | Marcus et al. | |
| 5,936,539 A | 8/1999 | Fuchs | |
| 5,942,986 A | 8/1999 | Shabot et al. | |
| 5,944,659 A | 8/1999 | Flach et al. | |
| 5,963,137 A | 10/1999 | Waters, Sr. | |
| 5,974,389 A | 10/1999 | Clark et al. | |
| 5,991,728 A | 11/1999 | DeBusk et al. | |
| 5,995,937 A | 11/1999 | DeBusk et al. | |
| 6,014,346 A | 1/2000 | Malone | |
| 6,014,633 A | 1/2000 | DeBusk et al. | |
| 6,057,758 A | 5/2000 | Dempsey et al. | |
| 6,057,782 A | 5/2000 | Koenig | |
| 6,067,019 A | 5/2000 | Scott | |
| 6,076,166 A | 6/2000 | Moshfeghi et al. | |
| 6,078,261 A | 6/2000 | Davsko | |
| 6,085,493 A | 7/2000 | DeBusk et al. | |
| 6,088,362 A | 7/2000 | Turnbull et al. | |
| 6,093,146 A | 7/2000 | Filangeri | |
| 6,097,308 A | 8/2000 | Albert et al. | |
| 6,111,509 A | 8/2000 | Holmes | |
| 6,125,350 A | 9/2000 | Dirbas | |
| 6,133,837 A | 10/2000 | Riley | |
| 6,147,592 A | 11/2000 | Ulrich et al. | |
| 6,183,417 B1 | 2/2001 | Geheb et al. | |
| 6,208,250 B1 | 3/2001 | Dixon et al. | |
| 6,241,668 B1 | 6/2001 | Herzog | |
| 6,259,355 B1 | 7/2001 | Chaco et al. | |

(56) References Cited

U.S. PATENT DOCUMENTS

| | | |
|---|---|---|
| 6,264,614 B1 | 7/2001 | Albert et al. |
| 6,272,347 B1 | 8/2001 | Griffith et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,868,256 B2 | 3/2005 | Dooley et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,885,288 B2 | 4/2005 | Pincus |
| 6,891,909 B2 | 5/2005 | Hurley et al. |
| 6,897,780 B2 | 5/2005 | Ulrich et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,958,706 B2 | 10/2005 | Chaco et al. |
| 7,038,588 B2 | 5/2006 | Boone et al. |
| 7,068,143 B2 | 6/2006 | Doering et al. |
| 7,079,036 B2 | 7/2006 | Cooper et al. |
| 7,092,376 B2 | 8/2006 | Schuman |
| 7,138,902 B2 | 11/2006 | Menard |
| 7,242,308 B2 | 7/2007 | Ulrich et al. |
| 7,292,135 B2 | 11/2007 | Bixler et al. |
| 7,315,535 B2 | 1/2008 | Schuman |
| 7,319,386 B2 * | 1/2008 | Collins et al. ............ 340/539.12 |
| 7,333,002 B2 * | 2/2008 | Bixler et al. ............ 340/286.07 |
| 7,336,187 B2 | 2/2008 | Hubbard, Jr. et al. |
| 7,443,302 B2 | 10/2008 | Reeder et al. |
| 7,464,425 B2 * | 12/2008 | Chambers et al. ................ 5/739 |
| 7,526,529 B2 | 4/2009 | Unluturk et al. |
| 7,538,659 B2 | 5/2009 | Ulrich et al. |
| 7,590,551 B2 | 9/2009 | Auer |
| 7,598,852 B2 | 10/2009 | Chriss |
| 7,612,679 B1 | 11/2009 | Fackler et al. |
| 7,715,387 B2 | 5/2010 | Schuman |
| 7,731,677 B2 * | 6/2010 | Sakurai .......... A61B 17/320068 |
| | | 604/22 |
| 7,746,218 B2 | 6/2010 | Collins, Jr. et al. |
| 7,831,447 B2 | 11/2010 | Schuman |
| 7,852,208 B2 | 12/2010 | Collins, Jr. et al. |
| 8,026,821 B2 | 9/2011 | Reeder et al. |
| 8,030,891 B2 * | 10/2011 | Welsch ................ A61M 5/142 |
| | | 320/112 |
| 8,046,625 B2 | 10/2011 | Ferguson et al. |
| 8,075,342 B1 * | 12/2011 | Harney et al. ............ 439/620.01 |
| 8,120,471 B2 | 2/2012 | Collins, Jr. et al. |
| 8,604,917 B2 * | 12/2013 | Collins et al. ............ 340/286.07 |
| 9,198,593 B2 * | 12/2015 | Lu ........................ A61B 5/0424 |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0044043 A1 | 4/2002 | Chaco et al. |
| 2002/0044059 A1 * | 4/2002 | Reeder et al. ............ 340/573.1 |
| 2002/0067273 A1 | 6/2002 | Jaques et al. |
| 2002/0070867 A1 | 6/2002 | Conway et al. |

(56) References Cited

U.S. PATENT DOCUMENTS

| | | | |
|---|---|---|---|
| 2002/0080037 A1 | 6/2002 | Dixon et al. | |
| 2002/0103674 A1 | 8/2002 | Reeder et al. | |
| 2002/0151990 A1 | 10/2002 | Ulrich et al. | |
| 2002/0173991 A1 | 11/2002 | Avitall | |
| 2002/0186136 A1 | 12/2002 | Schuman | |
| 2002/0196141 A1 | 12/2002 | Boone et al. | |
| 2003/0010345 A1 | 1/2003 | Koblasz et al. | |
| 2003/0028449 A1 | 2/2003 | Heinen et al. | |
| 2003/0030569 A1 | 2/2003 | Ulrich et al. | |
| 2003/0052787 A1* | 3/2003 | Zerhusen et al. | 340/573.1 |
| 2003/0074222 A1 | 4/2003 | Rosow et al. | |
| 2003/0146835 A1 | 8/2003 | Carter | |
| 2003/0149598 A1 | 8/2003 | Santoso et al. | |
| 2003/0176798 A1 | 9/2003 | Simon | |
| 2003/0206116 A1 | 11/2003 | Weiner et al. | |
| 2004/0015132 A1* | 1/2004 | Brown | 604/131 |
| 2004/0183681 A1 | 9/2004 | Smith | |
| 2004/0183684 A1 | 9/2004 | Callaway | |
| 2004/0186358 A1 | 9/2004 | Chernow et al. | |
| 2004/0193449 A1 | 9/2004 | Wildman et al. | |
| 2005/0035862 A1 | 2/2005 | Wildman et al. | |
| 2005/0185799 A1* | 8/2005 | Bertram | A61B 5/0002 381/67 |
| 2005/0242946 A1* | 11/2005 | Hubbard et al. | 340/539.12 |
| 2006/0049936 A1* | 3/2006 | Collins et al. | 340/539.11 |
| 2006/0214786 A1* | 9/2006 | Bixler et al. | 340/539.12 |
| 2006/0248221 A1 | 11/2006 | Hottel et al. | |
| 2007/0013511 A1* | 1/2007 | Weiner et al. | 340/539.12 |
| 2007/0083888 A1* | 4/2007 | Liebhold | H04N 5/44513 725/37 |
| 2007/0210917 A1 | 9/2007 | Collins, Jr. et al. | |
| 2008/0018436 A1 | 1/2008 | Traughber et al. | |
| 2008/0021731 A1 | 1/2008 | Rodgers | |
| 2008/0249470 A1* | 10/2008 | Malave et al. | 604/151 |
| 2009/0066486 A1* | 3/2009 | Kiekbusch et al. | 340/286.02 |
| 2009/0212925 A1 | 8/2009 | Schuman, Sr. et al. | |
| 2009/0212956 A1 | 8/2009 | Schuman et al. | |
| 2009/0214009 A1 | 8/2009 | Schuman, Sr. et al. | |
| 2009/0217080 A1 | 8/2009 | Ferguson et al. | |
| 2010/0079276 A1 | 4/2010 | Collins, Jr. et al. | |
| 2012/0029941 A1* | 2/2012 | Malave et al. | 705/3 |
| 2012/0069131 A1* | 3/2012 | Abelow | 348/14.01 |
| 2012/0092135 A1 | 4/2012 | Collins, Jr. et al. | |
| 2013/0045685 A1* | 2/2013 | Kiani | G08B 21/24 455/41.2 |
| 2013/0157571 A1* | 6/2013 | Wondka et al. | 455/41.2 |
| 2014/0009271 A1* | 1/2014 | Collins et al. | 340/286.07 |
| 2014/0316819 A1* | 10/2014 | Dunsirn | G06F 19/322 705/3 |

OTHER PUBLICATIONS

"The COMposer™ System, Installation Manual", by Hill-Rom Services Inc., (2003).225 pgs.

"COMLinx™ Enterprise Solutions, Nurse Communication Module, User's Guide", by Hill-Rom Services, Inc., (2000), 373 pgs.

"NaviCare Nurse Call User Manual", by Hill-Rom Services, Inc. (2008), 35 pgs.

"NaviCare Patent Flow System User Manual Version 5.2", by Hill-Rom Services, Inc. (2005), 99 pgs.

"NaviCare Patient Flow System User Manual Version 7.1", by Hill-Rom Services, Inc. (2008), 118 pgs.

"NaviCare Operations Management System User Manual Version 5.2", by Hill-Rom Services, Inc. (2005), 95 pgs.

"NaviCare Reporting User Manual", by Hill-Rom Services, Inc. (2007), 41 pgs.

\* cited by examiner

IN-ROOM ALARM CONFIGURATION OF NURSE CALL SYSTEM

BACKGROUND

The present disclosure relates to nurse call systems and particularly, to nurse call systems having the capability to couple to medical devices to receive generic alarm signals from the medical devices. More particularly, the present disclosure relates to configuring nurse call systems by caregivers.

Nurse call systems used in healthcare facilities are known. Some nurse call systems are equipped to receive alarm signals from medical equipment which couple to equipment ports provided in a hospital room, for example. Oftentimes, the alarms from the medical equipment are displayed at a master station as a generic alarm. The alarm is considered to be generic if there is no information about the type of alarm that is occurring or the type of medical equipment which is generating the alarm.

Some prior art nurse call systems permit maintenance technicians to make selections as to the types of alarms or equipment that are associated with particular alarms using a system configuration computer, such as a server. The server saves the configuration in a database and a subset of the database then gets transferred to other computer devices of the nurse call system. However, this manner of configuring the alarm or device types in a nurse call system is less than ideal because it requires the maintenance technician to reconfigure the system if any of the medical devices are disconnected from the system and replaced with a different type of device.

Other prior art nurse call systems permit a master station of the nurse call system to be used to configure alarm or device types for the equipment that is coupled to the nurse call system. However, configuring the alarm or device types at the master station is time consuming and either requires caregivers to coordinate with one another to set up the configuration or requires a caregiver that hooks up a piece of medical equipment in a room to walk to the master station to set up the alarm or device type on the master station computer. What is needed is an easier and more flexible way for caregivers to configure alarm or device types in a nurse call system.

SUMMARY

The present invention may comprise one or more of the features recited in the appended claims and/or the following features which each are considered to be optional and which, alone or in any combination, may comprise patentable subject matter:

A nurse call system may include a master station having a first electronic display. The nurse call system may have a room station which may be located in a patient room remote from the master station. The room station may have a second electronic display. The room station may be configured to communicate with the master station. The nurse call system may further include an equipment port located in the patient room and configured to couple to medical equipment to receive a signal from the medical equipment. The room station may be configured to present a list of medical equipment types on the second electronic display in response to coupling of the medical equipment to the equipment port for selection by a user of the type of medical equipment coupled to the equipment port.

In some embodiments, the signal comprises an alarm signal and/or a data signal, for example. Thus, the signal may include an alarm message that may be transmitted to the master station and that may include information identifying the selected medical equipment type in response to the signal being communicated to the equipment port from the medical equipment. The master station may display information about the alarm on the first electronic display and the information may include the selected medical equipment type. Alternatively or additionally, the master station also may display on the first electronic display at least one of a room number of the patient room from which the alarm message originated and the wait time before a caregiver responds to the alarm message.

According to some embodiments, at least one of the master station and room station may cause a page to be sent to at least one designated paging device in response to occurrence of the alarm signal. Alternatively or additionally, at least one of the master station and room station may cause a text message to be sent to at least one designated communication device carried by at least one caregiver in response to occurrence of the alarm signal. The at least one designated communication device may include, for example, at least one of a personal digital assistant (PDA), a telephone handset, and a cellular telephone.

The list of medical equipment types may include at least one of an IV pump, a call cord, a heart monitor, and a ventilator, but this list is certainly not intended to be exhaustive. Accordingly, the list of medical equipment types may include any type of equipment that is used in connection with patient care in healthcare facility and that includes an alarm output that is coupleable to other equipment.

According to this disclosure, the second electronic display may comprise a touchscreen display and the selection of the medical equipment type coupled to the equipment port may be accomplished by touching a field on the touchscreen display. Alternatively or additionally, the second electronic display may comprise an alphanumeric display with scrolling capability for selection of the medical equipment type.

The nurse call system may further include a control board communicatively coupled to the master station and the room station. The equipment port may be coupled to the control board. A face plate may be provided and the equipment port may be coupled to the face plate. A bed connection port to which a hospital bed may couple also may be coupled to the face plate. Alternatively or additionally, a pillow speaker connector to which a pillow speaker unit may couple also may be coupled to the face plate. Optionally, a nurse call cancel button also may be coupled to the face plate. In some embodiments, a second equipment port to which another medical device may be coupled also may be coupled to the face plate. In some embodiments, the equipment port comprises a ¼ inch jack. However, other types of equipment ports are within the scope of this disclosure and may include, for example, RJ-45 connectors, RS-232 ports, Universal Serial Bus (USB) ports, twisted wire pair connectors, coaxial connectors, and so on.

The nurse call system may further include an alert light located in proximity to the room and the alert light may be illuminated in response to the alarm signal. In some embodiments, the nurse call system may include a control board that may receive an alarm message associated with the alarm signal and that may control the illumination of the alert light. It is contemplated by this disclosure that the alert light may be included as part of a dome light assembly.

According to an aspect of this disclosure, a nurse call system may include a room station that may be located in a patient room and that may have an electronic display. The nurse call system may further include an equipment port that may be located in the patient room and that may be configured to couple to medical equipment to receive a signal from the medical equipment. The room station may be configured to present a list of medical equipment types on the second graphical display in response to coupling of the medical equipment to the equipment port for selection by a user of the type of medical equipment coupled to the equipment port.

According to another aspect of this disclosure, a nurse call system may include a room station that may be located in a patient room and that may have an electronic display. A plurality of equipment ports may be located in the patient room. Each of the plurality of equipment ports may be configured to couple to medical equipment to receive signals from the medical equipment. The room station may be configured to present a list of medical equipment types on the electronic display in response to coupling of the medical equipment to a selected equipment port of the plurality of equipment ports for selection by a user of the type of medical equipment coupled to the selected equipment port.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
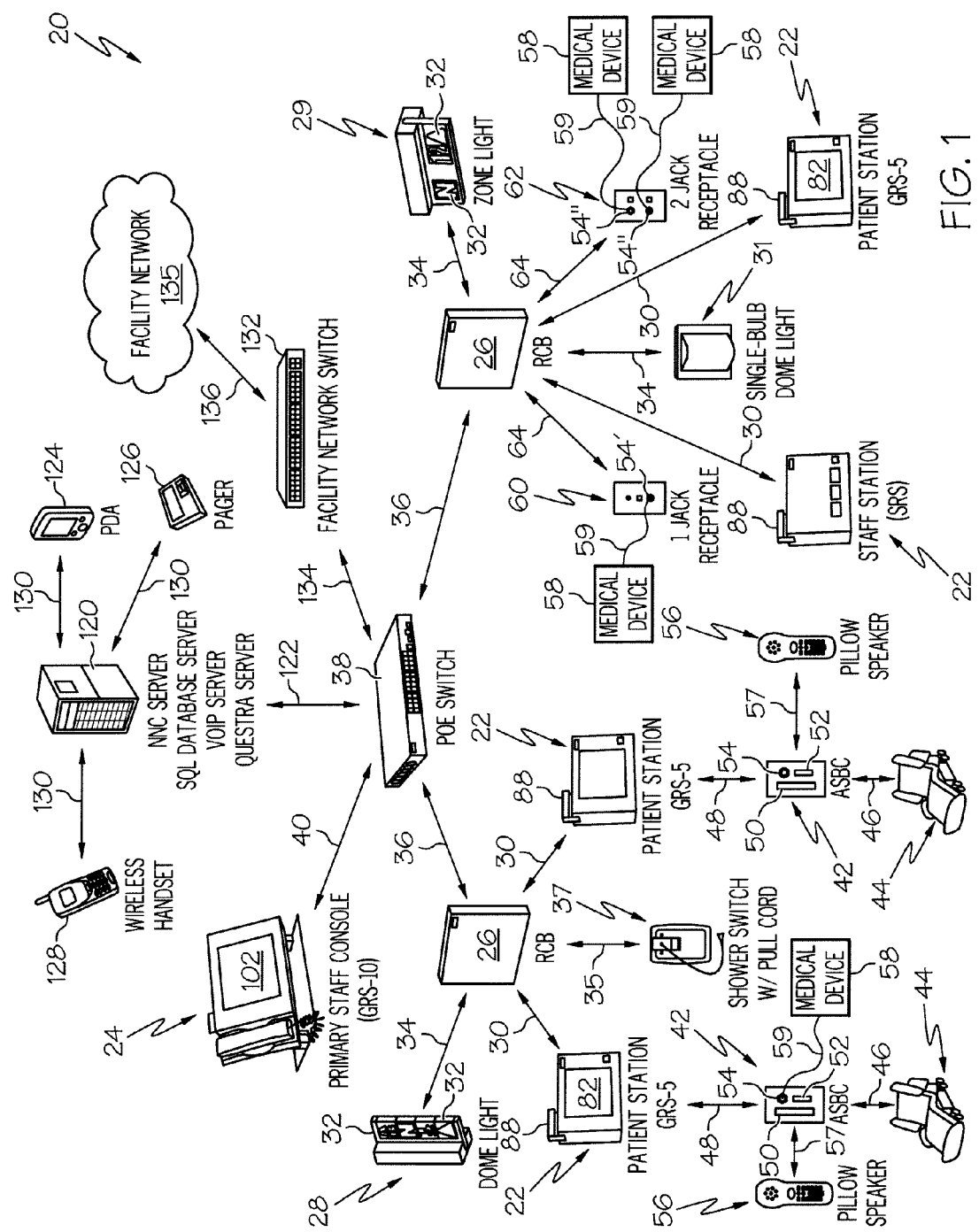
FIG. 1 is a block diagram of a healthcare communication system including a nurse call system having a primary staff console coupled to a number of patient stations via a PoE switch and room control boards (RCB) units and having a number of medical devices coupled to either the patient stations or RCB units via an audio station bed connector (ASBC) unit, a 1 jack receptacle, and a 2 jack receptacle, each of which has at least one equipment port to which the respective medical devices couple.

A healthcare communication system 20 includes a plurality of patient stations or room stations 22 and a primary station or console 24 which are communicatively coupled as shown diagrammatically in FIG. 1. Many of the stations 22 are located in patient rooms and are mounted, for example, to a wall of the respective room or to a headwall unit that, in turn, is mounted to a wall of the respective room. Stations 22 may be mounted to other architectural support structures, such as service chases or columns just to name a couple. Thus, stations 22 are referred to interchangeably as "patient stations" or "room stations" or just "stations." Station 24 is referred to herein interchangeably as a "primary console" or "master station" or just "station." Stations 22 may be located in other areas of the healthcare facility as well, such as in staff work areas including, for example, hallways and staff lounges. The stations 22 located in staff work areas are generally referred to as "staff stations." Stations 22 may also sometimes be referred to herein as "graphical audio stations." The functionality of stations 22 described herein is applicable to all of stations 22 regardless of whether the station 22 is a room station 22 or a staff station 22, unless specifically noted otherwise.

Patient stations 22 communicate bidirectionally (e.g., two-way communication) with a room control board (RCB) unit 26 which includes an input/output (I/O) circuit contained within a housing of the RCB unit 26. The bidirectional communication between stations 22 and units 26 are indicated diagrammatically in FIG. 1 by double headed arrows 30. Various alert light devices are activated by the I/O circuit of the RCB unit 26 when a certain alert or alarm condition occurs. The terms "alarm" and "alert" are used interchangeably herein and each is considered to encompass the broad meanings of both. Illustrative examples of these alert light devices include a dome light assembly 28, a zone light assembly 29, and a single-bulb dome light assembly 31 as shown in FIG. 1. As also shown in the illustrative example, a shower switch with pull cord 37 is coupled to one of the RCB units 26 as indicated by double headed arrow 35. Pull cord 37 is pulled by a patient in the bathroom or shower to send out an alarm signal.

Assemblies 28, 29 each have multiple indicia 32 which are illuminated individually by associated lights (e.g., light emitting diodes) depending upon the particular type of alert or alarm condition that occurs. As its name implies, the single-bulb dome light assembly 31 has only a single light that is illuminated when any monitored alarm or alert condition occurs. Assemblies 28, 29, 31 are each coupled to a respective RCB unit 26 as shown diagrammatically in FIG. 1 with double headed arrows 34. Dome light assemblies 28, 29, 31 are typically mounted outside respective patient rooms near the doorways of the rooms and are readily visible to caregivers in the hallway to determine whether any calls or other events indicated on the dome light are occurring within the associated room.

RCB units 26 each communicate bidirectionally with a Power over Ethernet (PoE) switch 38 as indicated diagrammatically in FIG. 1 by double headed arrows 36. PoE switch 38 communicates bidirectionally with master station 24 as indicated diagrammatically by double headed arrow 40. Suitable PoE switches are available from a variety of suppliers and may include, for example, the PoE switch marketed by Hill-Rom Company, Inc. in connection with its NaviCare® Nurse Call™ system or such as one or more of the various Dell PoE switches marketed under the PowerConnect™ brand name. While only three patient stations 22 and one staff station 22 are shown in FIG. 1 as being communicatively coupled to master station 24, via two RCB units 26 and via PoE switch 38, it will be appreciated that system 20 may have numerous such patient stations 22 and multiple staff stations 22 that may communicate with master station 24 via respective RCB units 26 and via one or more PoE switches 38.

In some embodiments, such as the one shown in FIG. 1, system 20 includes audio station bed connector (ASBC) units 42, each of which is communicatively coupled to an associated hospital bed 44 via double headed arrows 46 as shown diagrammatically in FIG. 1. ASBC units 42 are, in turn, coupled to a respective patient station 22 as indicated diagrammatically in FIG. 1 via double headed arrows 48. In some other embodiments, one or more of ASBC units 42 may be coupled to RCB unit 26 without being coupled to one of the patient stations 22. In still other embodiments, ASBC units 42 may be integrated into a common housing of graphical audio stations 22.

In the illustrative embodiment, each ASBC unit 42 includes a 37-pin connector or port 50 to attach to a bed cable, includes a second connector or port 52 for attachment of a call pendant or pillow speaker unit 56, and includes a third port 54, such as a ¼ inch jack, to which a medical device 58 couples. Pillow speaker units 56 coupled to ports 52 with suitable cables or cords as indicated by double headed arrows 57 in FIG. 1. Connection of medical device 58 to port 54 permits alarms from medical device 58 to be communicated to patient station 22 and then to master station 24 via RCB unit 26 and PoE switch 38. Numerous types of medical devices 58 are coupleable to port 54. Examples of some such medical devices include intravenous (IV) fluid pumps, electrocardiographs (EKG's), blood gas monitors (e.g., SpO2 monitors), electroencephalographs (EEG's), blood pressure monitors, ventilators, and respiration monitors, just to name a few.

Medical devices 58 are typically configured to output a general alarm at a respective output port and this general alarm is communicated to port 54 of ASBC unit 42 when the medical device 58 is coupled to port 54 by a suitable conductor or cable 59, shown diagrammatically in FIG. 1. Unlike in prior art nurse call systems, stations 22 are used to specify or designate the type of equipment that is coupled to port 54 of units 42. This is an improvement over prior art nurse call systems in which master station 24 is used to specify or designate the equipment type. The manner in which stations 22 are used in this regard is described in further detail below in connection with FIGS. 7 and 8.

Figure 2:
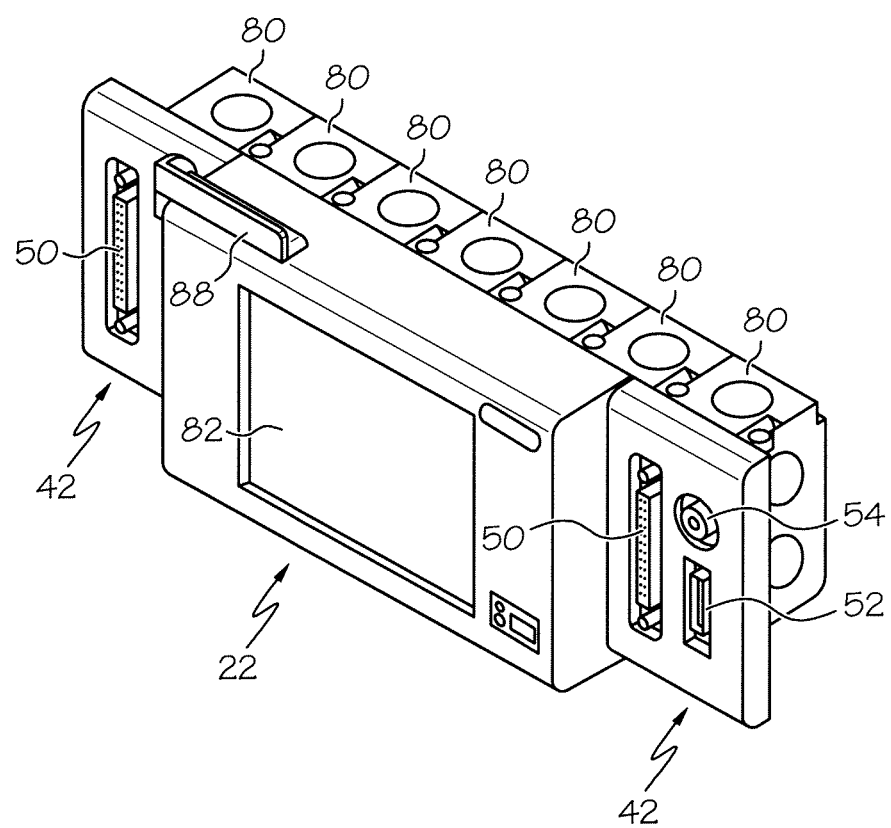
FIG. 2 is an isometric view showing one of the patient stations having ASBC units on either side thereof.

Referring now to FIG. 2, a patient station 22 is shown with ASBC units 42 mounted to either side thereof. A number of electrical junction boxes or back boxes 80 associated with the station 22 and units 42 are ganged together. It should be appreciated that boxes 80 are received within a recess or space provided in a wall or headwall unit or whatever architectural structure to which station 22 and units 42 are mounted. In this arrangement, a single patient station 22 is able to be used in a patient room that has two hospital beds 44. One hospital bed 44 couples to port 50 of one of units 42 and the other hospital bed 44 couples to port 50 of the other of units 42. Information regarding alerts or alarms from these two hospital beds 44 is displayed on a graphical display screen 82 of patient station 22 in addition to being displayed at the associated master station 24. Similarly, if medical equipment 58 is coupled to port 54 of both units 42, then alerts or alarms from the medical equipment 58 is displayed on graphical display screen 82. Furthermore, graphical display screen 82 is used to specify or designate the type of medical equipment 58 that is coupled to the two ports 54 of the FIG. 2 arrangement.

It is within the scope of this disclosure for medical devices 58 to couple to other types of connector devices different from the ASBC units 42 shown in FIGS. 1 and 2. One such device is a 1-jack receptacle 60, shown in FIGS. 1 and 3, and another such device is a 2-jack receptacle 62, shown in FIGS. 1 and 5. Receptacle 60 includes a single port 54' to which a medical device 58 couples via cable 59 and receptacle 62 includes a pair of ports 54" to which respective medical devices 58 couple via respective cables 59 as shown diagrammatically in FIG. 1. In the illustrative example, ports 54, 54', 54" are all constructed similarly such that cable 59 can be used to couple medical devices 58 to any of units 42 and receptacles 60, 62, as desired. In other embodiments, ports 54, 54', 54" are constructed differently from one another such that different types of cables 59 are needed for coupling medical equipment 58 to these various types of ports 54, 54', 54".

In the illustrative example, each of receptacles 60, 62 is coupled electrically to one of the RCB units 26 as indicated diagrammatically in FIG. 1 by double headed arrows 64. The patient station 22 coupled to this same RCB unit 26 is used to indicate the type(s) of medical devices 58 coupled to respective ports 54', 54" of receptacles 60, 62. That patient station 22 has a graphical display screen 82, whereas the staff station 22 coupled to the same RCB unit 26 in the illustrative example does not. It is contemplated by this disclosure, however, that staff station 22 may also have a display screen 82 which may be used for designating the type(s) of medical devices 58 coupled to ports 54', 54", although using patient stations 22 for this purpose makes more sense since patient stations 22 will typically be located in the same room in which devices 58 are coupled to ports 54', 54" whereas staff stations 22 typically will not be.

Figure 3:
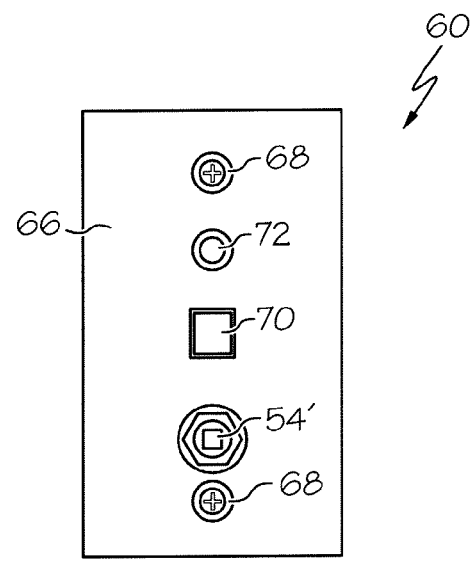
FIG. 3 is front elevation view of the 1 jack receptacle.
Figure 4:
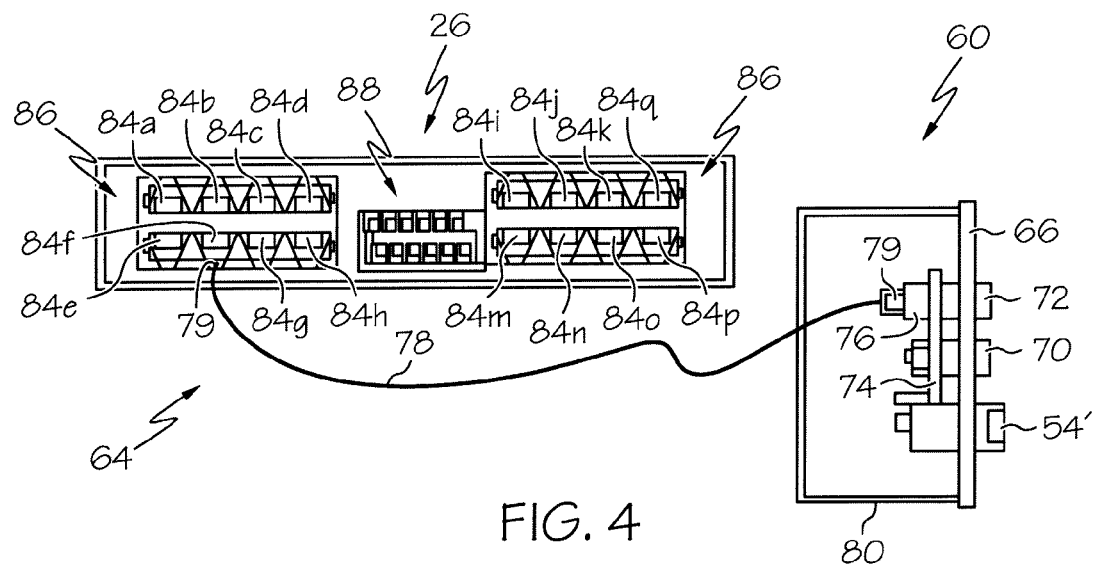
FIG. 4 is a diagrammatic view showing the 1 jack receptacle mounted to a box and connected to one of the RCB's.

Referring now to FIGS. 3 and 4, receptacle 60 includes a face plate 66 that couples to an associated back box 80 with one or more suitable fasteners such as the pair of illustrative screws 68. Receptacle 60 also includes a call cancel/cable disconnect button 70 and a visual indicator 72. Button 70 is pressed by a caregiver when disconnecting cable 59 from port 54' to prevent a cable disconnect signal from being triggered or to cancel an alarm that is being sent by equipment 58 to port 54' via cable 59. When canceled, the alarm is blocked by the RCB unit 26 and prevented from being forwarded to rest of system 20.

Visual indicator 72 is a light emitting diode (LED) in some embodiments and is illuminated to indicate the alarm status being communicated to port 54' by equipment 58. For example, in some embodiments, indicator 72 is turned off when no alarm occurs and is turned on when an alarm occurs. Indicator 72 may shine red or amber when turned on in some embodiments. In other embodiments, indicator 72 shines a first color (e.g., green) when no alarm condition is occurring and shines a second color (e.g., red or amber) when an alarm condition occurs.

Port 54', button 70, and indicator 72 are coupled to a circuit board 74 that is situated behind face plate 66 as shown in FIG. 4. Port 54', button 70, and indicator 72 project through, or are at least accessible through, corresponding apertures formed in face plate 66. A connector 76 is also coupled to circuit board 74. The data link 64 between receptacle 60 and RCB unit 26 is a UTP5 cable 78 with RJ-45 connectors 79 in the illustrative example, but other types of cabling and connectors are within the scope of this disclosure. One of connectors 79 attaches to connector 76 of receptacle 60 and the other connector 79 couples to a connector 84f of one connector bank 86 of a pair of connector banks 86 that are situated on opposite sides of a terminal block 88 of RCB unit 26.

The connector banks 86 of the illustrative RCB unit 26 of FIG. 4 correspond to the connector banks 86 used in Hill-Rom's NaviCare® Nurse Call™ system. Other nurse call systems within the scope of this disclosure have RCB units 26 configured differently, or have other hardware components altogether (e.g., RCB unit 26 functionality integrated into station 22). In any event, in the illustrative example, connectors 84a, 84b, 84c, 85d, 84e, 84f, 84g are for coupling of remote switches (e.g., pull cord 37), equipment receptacles (e.g., ports 54, 54', 54"), and supervised interface modules (e.g., other devices that generate alarm calls such as smoke detectors); connectors 84h, 84m are for coupling of first and second bed interface units (BIU's) which are similar to ASBC units 42 but which connect to RCB units 26 directly rather than through station(s) 22; connector 84*i* is for coupling of a room location receiver (RLR) which is part of a locating and tracking system that receives wireless signals from a tag or badge coupled to caregivers or equipment; connector 84*j* is for coupling to dome light assembly 28; connector 84*n* is for coupling to zone light assembly 29; connectors 84*k*, 84*o* are for coupling to stations 22; connector 84*q* is for coupling to PoE switch 38; and connector 84*p* is for coupling either to master station 24 or to another RCB unit 26 to form a daisy-chained arrangement of RCB units 26. Based on the foregoing, it should be appreciated that connector 79 at the end of cable 78 distal from receptacle 60 could be coupled to any of connectors 84*a-g* in the illustrative example. The terminal block 88 is used for coupling to single-bulb dome light 31 and to other equipment such as a Stat Clock/Timer which indicates the amount of time since a "code blue" (e.g., patient cardiac arrest) was called such as by pulling on a code blue call lever 88 of stations 22.

Figure 5:
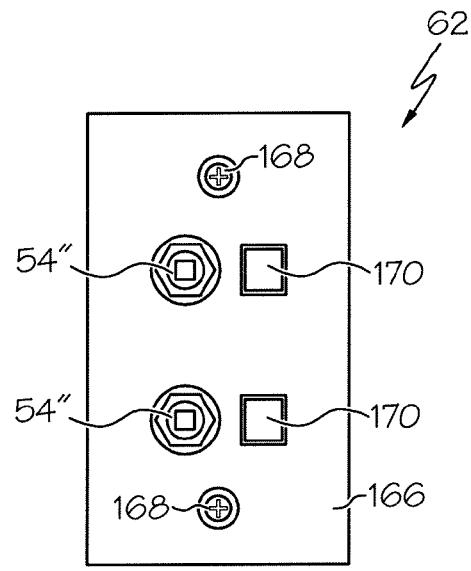
FIG. 5 is a front elevation view of the 2 jack receptacle.
Figure 6:
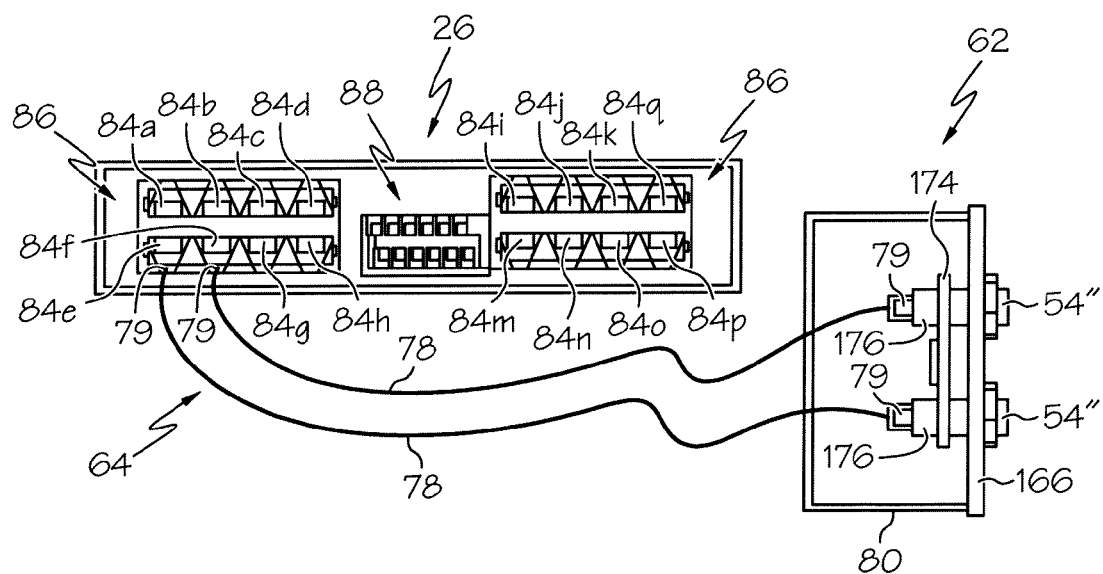
FIG. 6 is a diagrammatic view showing the 2 jack receptacle mounted to a box and connected to one of the RCB's.

Referring now to FIGS. 5 and 6, receptacle 62 includes a face plate 166 that couples to an associated back box 80 with one or more suitable fasteners such as the pair of illustrative screws 168. Receptacle 62 also includes a pair of call cancel/cable disconnect button 170, each of which is situated alongside an associated one of the ports 54". Unlike receptacle 60, receptacle 62 does not have any visual indicators in the illustrative embodiment. However, it is within the scope of this disclosure for receptacle 62 to include a pair of visual indicators, one each for the two ports 54" of receptacle 62. Each of buttons 170 is pressed by a caregiver when disconnecting cable 59 from the associated port 54" to prevent a cable disconnect signal from being triggered or to cancel an alarm that is being sent by equipment 58 to port 54" via cable 59. Pressing either of buttons 170 causes RCB to block the associated alarm to prevent the alarm from being forwarded on to the rest of system 20.

Ports 54" and buttons 170 are coupled to a circuit board 174 that is situated behind face plate 166 as shown in FIG. 6. Ports 54" and buttons 170 project through, or are at least accessible through, corresponding apertures formed in face plate 166. A pair of connectors 176 is also coupled to circuit board 74. The data link 64 between ports 54" of receptacle 62 and RCB unit 26 is a pair of UTP5 cables 78, each with RJ-45 connectors 79 in the illustrative example, but other types of cabling and connectors are within the scope of this disclosure. Connector 79 at one end of each of cables 78 attaches to a respective connector 176 of receptacle 62 and the connector 79 at the other end of each of cables 78 couples to connectors 84*e*, 84*f* of one connector bank 86 of RCB unit 26 in the illustrative example. The discussion above of connector banks 86 and terminal block 88 in connection with FIG. 4 is equally applicable to FIG. 6 and is not repeated.

Figure 7:
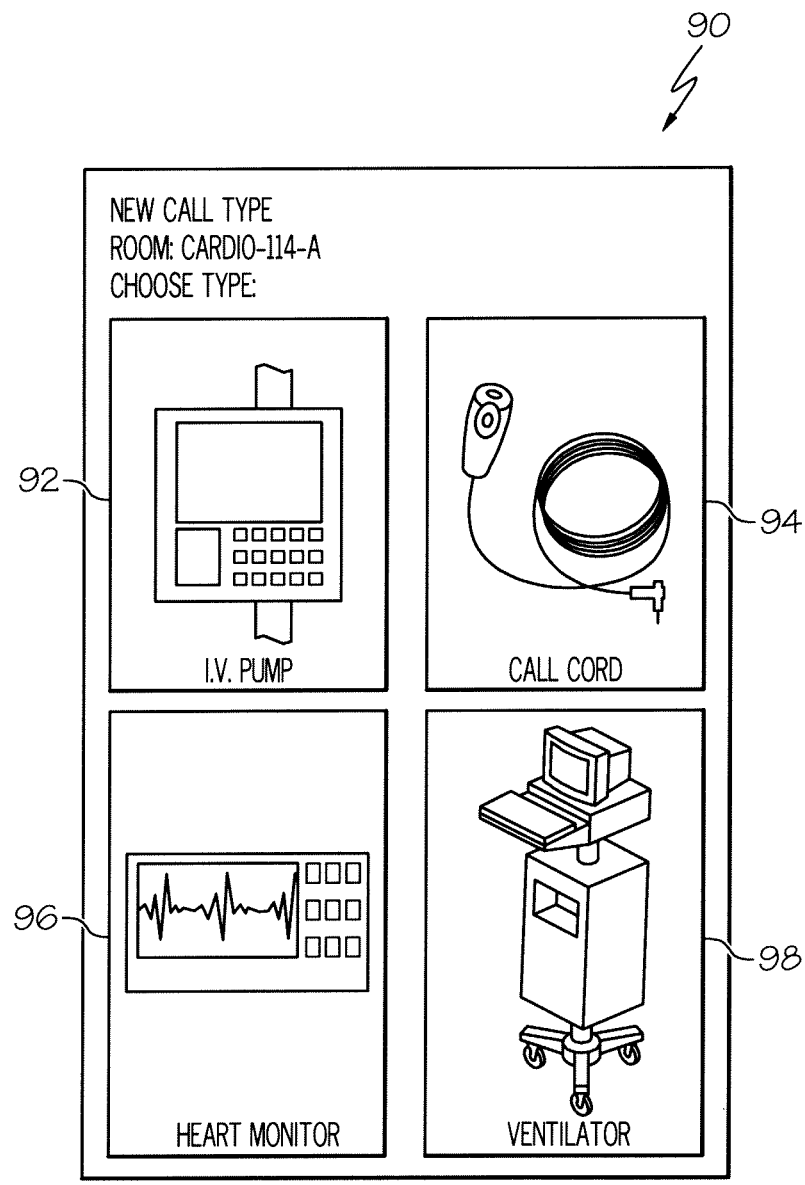
FIG. 7 is a screen shot of alarm selection screen that appears on a graphical display screen of one of the patient stations in response to connection of a medical device to an equipment port associated with the patient station.

Based on the foregoing discussion, it should be appreciated that medical devices 58 of a variety of different types are coupleable to ports 54, 54', 54" of ASBC units 42 and receptacles 60, 62. In response to each medical device 58 being coupled to a corresponding port 54, 54', 54", the circuitry and programming of the associated station 22 cause an alarm selection screen 90, an example of which is shown in FIG. 7, to appear on graphical display screen 82 of the associated station 22. In the illustrative example, an I.V. pump field 92, a call cord field 94, a heart monitor field 96 and a ventilator field 98 appears on screen 90. Each field 92, 94, 96, 98 includes a graphical image and text to indicate to the caregiver the choices which are available for the user to designate to the medical equipment 58 which has just been connected to one of ports 54, 54', 54".

In the upper left header area of screen 90, the text "NEW CALL TYPE" appears in a first line of text to indicate to the caregiver that a new call type needs to be chosen, the text "ROOM: CARDIO-114-A" appears in a second line of text to indicate to the caregiver the room number to be associated with the new call type, and the text "CHOOSE TYPE:" appears in a third line of text just above field 92 in the illustrative example. The room number, of course, will vary room by room within any given healthcare facility and the formatting of the room number will vary from facility to facility. Furthermore, fields that correspond to other device types are contemplated by this disclosure. If the total number of device type fields are too numerous to fit on a single screen on graphical display 82, then a vertical and/or horizontal scroll bar is provided on screen 90 to permit the caregiver to navigate to the other fields. The caregiver touches one of fields 92, 94, 96, 98 (or any other fields that are available) to choose the call type which is then allocated or designated to the particular port 54, 54', 54" for the newly connected medical device 58.

Figure 8:
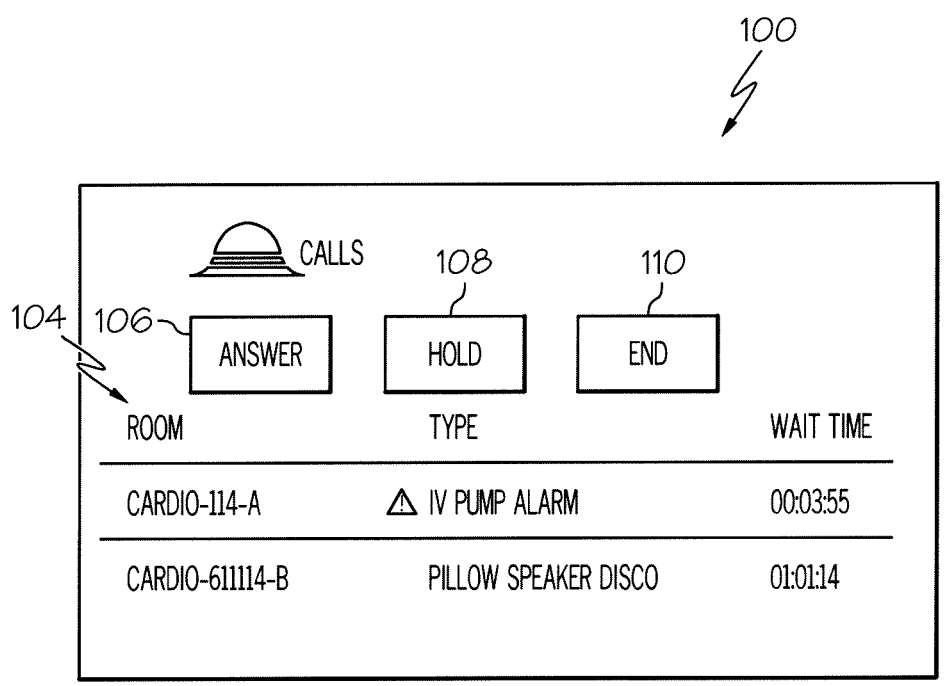
FIG. 8 is a screen shot of an alarm display screen that appears on a graphical display screen of the primary console in response to a medical device alarm of a medical device that has been set up using an associated patient station.

Referring now to FIG. 8, an alarm display screen 100 which appears on a graphical display screen 102 of the primary console 24 in response to one or more alerts or alarms occurring in system 20, including alarms or alerts originating on medical devices 58, is shown. When medical device 58 sends an alarm or alert message to port 54, 54', 54" via cable 59, station 22 and/or RCB unit 26 (depending upon the configuration), transmits information regarding the alert/alarm, including the designated alarm type, to primary console 24 via PoE switch 38. In the illustrative example, screen 100 has an alarm table 104 with a Room column, Type column, and Wait Time column. For each alarm, the room from which the alarm is originating appears in the Room column, the type of device generating the alarm appears in the Type column, and the amount of time that has transpired since the beginning of the alarm appears in the Wait Time column.

The information appearing in the Type column corresponds to the designation made by a caregiver when initially configuring the medical device alarm information using screen 90 at the corresponding station 22. Thus, based on information in the first row of table 104 in the illustrative example, an IV pump alarm has been occurring in room Cardio-114-A for three minutes, fifty five seconds. In the FIG. 8 example, information relating to a second alarm appears in row two of table 104.

As also shown in FIG. 8, screen 100 has an Answer icon or button 106, a Hold icon or button 108, and an End icon or button 110. A caregiver is able to select a row of table 104 and then press Answer icon 106 to establish a voice communication link with the room station 22 of the particular room associated with the row chosen on table 104. If the caregiver wishes to establish a voice communication link with another room, the caregiver selects Hold icon 108 while the existing row of table 104 is selected and then the caregiver selects a new row to establish voice communications with the room corresponding to that newly selected row. If the caregiver at master station 24 is finished with his or her voice communication with the room associated with the selected row, then the caregiver selects the End icon 110.

Referring again to FIG. 1, illustrative system 20 has one or more servers 120 coupled to PoE switch 38 by an appropriate data link as indicated by double headed arrow 122. Server 120 may comprise one or more of a nurse call server, an SQL database server, a voice over Internet protocol (VoIP) server, and a Questra server, for example. In the illustrative example, server 120 facilitates communication between other devices within network 20 and portable wireless devices that are carried by caregivers. Illustratively, the portable wireless devices carried by caregivers include a personal digital assistant (PDA) 124, a pager 126, and a wireless telephone handset 128. Cellular telephones are considered to be wireless telephone handsets 128 according to this disclosure. The double headed arrows 130 illustrated between server 120 and portable wireless devices 124, 126, 128 in FIG. 1 are intended to diagrammatically represent the infrastructure that provides the communication or data link between devices 124, 126, 128 and server 120.

In some embodiments, primary console 24 is used to select which alarms from medical equipment 58 are to be forwarded on to the portable wireless communication device 124, 126, 128 carried by caregivers who are assigned to the patient associated with the medical device 58 generating the alarm. See, for example, U.S. Pat. Nos. 7,319,386; 7,746,218; and 8,120,471 and U.S. Patent Application Publication No. 2012/0092135 A1, each of which is hereby incorporated herein by this reference to the extent that they are consistent with this disclosure which shall control as to any inconsistencies, for a discussion of configuring a nurse call system to send designated alarms to portable wireless communication devices carried by caregivers.

PoE switch 38 is coupled to the remainder of the facility network 135 via a facility network switch 132 and data links 134, 136 in the illustrative example of FIG. 1. Thus, data from beds 44 and medical devices 58, for example, is able to be communicated to other systems found in a healthcare setting such an electronic medical records (EMR) system or admit/discharge/transfer (ADT) system. Furthermore data from those other systems is able to be communicated to stations 22, 24, beds 44 and medical devices 58. Thus, alarms occurring on medical devices 58 may be communicated to the EMR system for charting in a patient's medical record, for example. The alarm type communicated to the EMR system is the type that has been established using the accompanying station 22.

According to this disclosure, each of the communications links or data links 30, 34, 36, 40, 46, 48, 50, 54, 60, 62, 66, 134, 136 shown diagrammatically by lines or arrows in FIG. 1 may include wired links and/or wireless links and/or combinations thereof, along with associated hardware, software, and connectors. For example, with regard to links 46 between beds 44 and ASBC units 42, known cables having 37-pin connectors (or similar connectors) may provide these links 44. Alternatively or additionally, some of links 46 may be wireless links, in which case, the respective beds 44 and units 42 have appropriate wireless transmitter and wireless receiver circuitry, which may be in the form of a wireless transceiver. Such wireless communication between beds 44 and units 42 is discussed, for example, in U.S. Pat. Nos. 7,852,208; 7,319, 386 and in U.S. Patent Application Publication No. 2007/0210917 A1, each of which is hereby incorporated herein by this reference to the extent that they are consistent with this disclosure which shall control as to any inconsistencies.

It is also contemplated that the communication protocol for links 30, 34, 36, 40, 46, 48, 50, 54, 60, 62, 66, 134, 136 may be according to any suitable protocol such as the TCP/IP protocol, the RS-232 protocol, the RS-422 protocol, the RS-423 protocol, or the RS-485 protocol, or similar such protocols, and such as wireless protocols including any of the IEEE 802.11$_x$ protocols (where x represents the various revision levels a, b, c, d, e, g and so forth of the 802.11 protocol), the Bluetooth protocol, the Zigbee protocol, or similar such wireless communication protocols.

While stations 22, 24 are disclosed herein as having graphical display screens that are touch screens, for example, it is within the scope of this disclosure for stations 22, 24 to have other types of electronic displays. Thus, the term "electronic display" is intended to cover all types of displays that are capable of producing images of alphanumeric characters including graphical display screens such as touch screen displays.

While the term "server" is used herein, it will be understood by those skilled in the art that the functionality represented or performed by devices referred to as "severs" may comprise and be performed by any suitable computer device having software programs or services that may be resident and/or executable by any computer, device or equipment in the system or more than one computer, device or equipment in the network. Thus, there term "server" is intended to broadly encompass any computer device that is capable of performing the mentioned functions.

The architecture of system 20 shown in FIG. 1 is simply one diagrammatic example and the teachings of this disclosure are intended to be applicable to all types of healthcare information technology systems, including nurse call systems, regardless of architecture. Examples of other configurations of such systems are shown, for example, in the patents and published applications already incorporated by reference herein; in U.S. Pat. Nos. 8,046,625; 8,026,821; 7,831,447; 7,715,387; 7,538,659; 7,443,302; 7,315,535; 7,242,308; 7,092,376; 6,897,780; 6,876,303; 6,362,725; 6,147,592; 5,838,223; 5,561,412; and 5,699,038; and in U.S. Patent Application Publication Nos. 2009/0214009 A1; 2009/0212956 A1; and 2009/0212925 A1; each of which is hereby incorporated herein by this reference to the extent that they are consistent with this disclosure which shall control as to any inconsistencies.

Although certain illustrative embodiments have been described in detail above, many embodiments, variations and modifications are possible that are still within the scope and spirit of this disclosure as described herein and as defined in the following claims.

The invention claimed is:

1. A nurse call system comprising
   a master station having a first electronic display,
   a room station located in a patient room remote from the master station and having a second electronic display, the room station being configured to communicate with the master station, the room station including a code blue call lever that is spaced from the second electronic display and that is moved manually to send a code blue call signal to the master station, and
   an equipment port located in the patient room and configured to couple to medical equipment via a cable of the medical equipment to receive a signal via the cable from the medical equipment, the medical equipment being other than a patient bed, the equipment port being mounted in the patient room and spaced apart from each of the room station, the patient bed, and the medical equipment, wherein the signal is a generic alarm signal that is devoid of any information that identifies the piece of medical equipment, wherein the room station is configured to present a list of medical equipment types on the second electronic display in response to coupling of the medical equipment to the equipment port for selection by a user of the type of medical equipment coupled to the equipment port.

2. The nurse call system of claim 1, wherein an alarm message is transmitted to the master station including information selected on the room station identifying the selected medical equipment type in response to the generic alarm signal being communicated to the equipment port from the medical equipment.

3. The nurse call system of claim 2, wherein the master station displays information about the alarm signal on the first electronic display including displaying the selected medical equipment type.

4. The nurse call system of claim 3, wherein the master station also displays on the first electronic display at least one of a room number of the patient room from which the alarm message originated and the wait time before a caregiver responds to the alarm message.

5. The nurse call system of claim 2, wherein at least one of the master station and the room station cause a page to be sent to at least one designated paging device in response to occurrence of the generic alarm signal.

6. The nurse call system of claim 2, wherein at least one of the master station and room station cause a text message to be sent to at least one designated communication device carried by at least one caregiver in response to occurrence of the generic alarm signal.

7. The nurse call system of claim 6, wherein the at least one designated communication device comprises at least one of a personal digital assistant (PDA), a telephone handset, and a cellular telephone.

8. The nurse call system of claim 1, wherein the list of medical equipment types includes at least one of an IV pump, a call cord, a heart monitor, and a ventilator.

9. The nurse call system of claim 1, wherein the second electronic display comprises a touchscreen display and the selection of the medical equipment type coupled to the equipment port is accomplished by touching a field on the touchscreen display.

10. The nurse call system of claim 1, further comprising a control board communicatively coupled to the master station and the room station and the equipment port being coupled to the control board.

11. The nurse call system of claim 1, further comprising a face plate, the equipment port being coupled to the face plate, and a bed connection port to which a hospital bed couples also being coupled to the face plate.

12. The nurse call system of claim 11, further comprising a pillow speaker connector to which a pillow speaker unit couples also being coupled to the face plate.

13. The nurse call system of claim 1, further comprising a face plate, the equipment port being coupled to the face plate, and a nurse call cancel button also being coupled to the face plate.

14. The nurse call system of claim 1, further comprising a face plate, the equipment port being coupled to the face plate, and a second equipment port to which another medical device is coupleable also being coupled to the face plate.

15. The nurse call system of claim 1, wherein the equipment port comprises a ¼ inch jack.

16. The nurse call system of claim 1, further comprising an alert light located in proximity to the room and the alert light being illuminated in response to the generic alarm signal.

17. The nurse call system of claim 16, further comprising a control board that receives an alarm message associated with the generic alarm signal and that controls the illumination of the alert light.

18. The nurse call system of claim 16, wherein the alert light is included as part of a dome light assembly.

19. The nurse call system of claim 1, wherein the second electronic display comprises an alphanumeric display with scrolling capabilities for selection of the medical equipment type.

20. A nurse call system comprising
a room station located in a patient room and having an electronic display, the room station including a code blue call lever that is spaced from the second electronic display and that is moved manually to send a code blue call signal, and
an equipment port located in the patient room and configured to couple to medical equipment via a cable of the medical equipment to receive a signal via the cable from the medical equipment, the medical equipment being other than a patient bed, the equipment port being mounted in the patient room and spaced apart from each of the room station, the patient bed, and the medical equipment, wherein the signal is a generic alarm signal that is devoid of any information that identifies the medical equipment, wherein the room station is configured to present a list of medical equipment types on the electronic display in response to coupling of the medical equipment to the equipment port for selection by a user of the type of medical equipment coupled to the equipment port.

21. A nurse call system comprising
a room station located in a patient room and having an electronic display, the room station including a code blue call lever that is spaced from the second electronic display and that is moved manually to send a code blue call signal, and
a plurality of equipment ports located in the patient room, each of the plurality of equipment ports being configured to couple to medical equipment via a cable of each piece of medical equipment to receive signals via the cables from the respective medical equipment, the medical equipment being other than a patient bed, each equipment port of the plurality of equipment ports being mounted in the respective patient room and spaced apart from each of the respective room station, the respective patient bed, and the respective medical equipment, wherein the signals are generic alarm signals that are devoid of any information that identifies the respective medical equipment, wherein the room station is configured to present a list of medical equipment types on the electronic display in response to coupling of the medical equipment to a selected equipment port of the plurality of equipment ports for selection by a user of the type of medical equipment coupled to the selected equipment port.

* * * * *